Aug. 30, 1949. G. MERRILL Plant Pat. 869
PEACH TREE
Filed Aug. 28, 1948
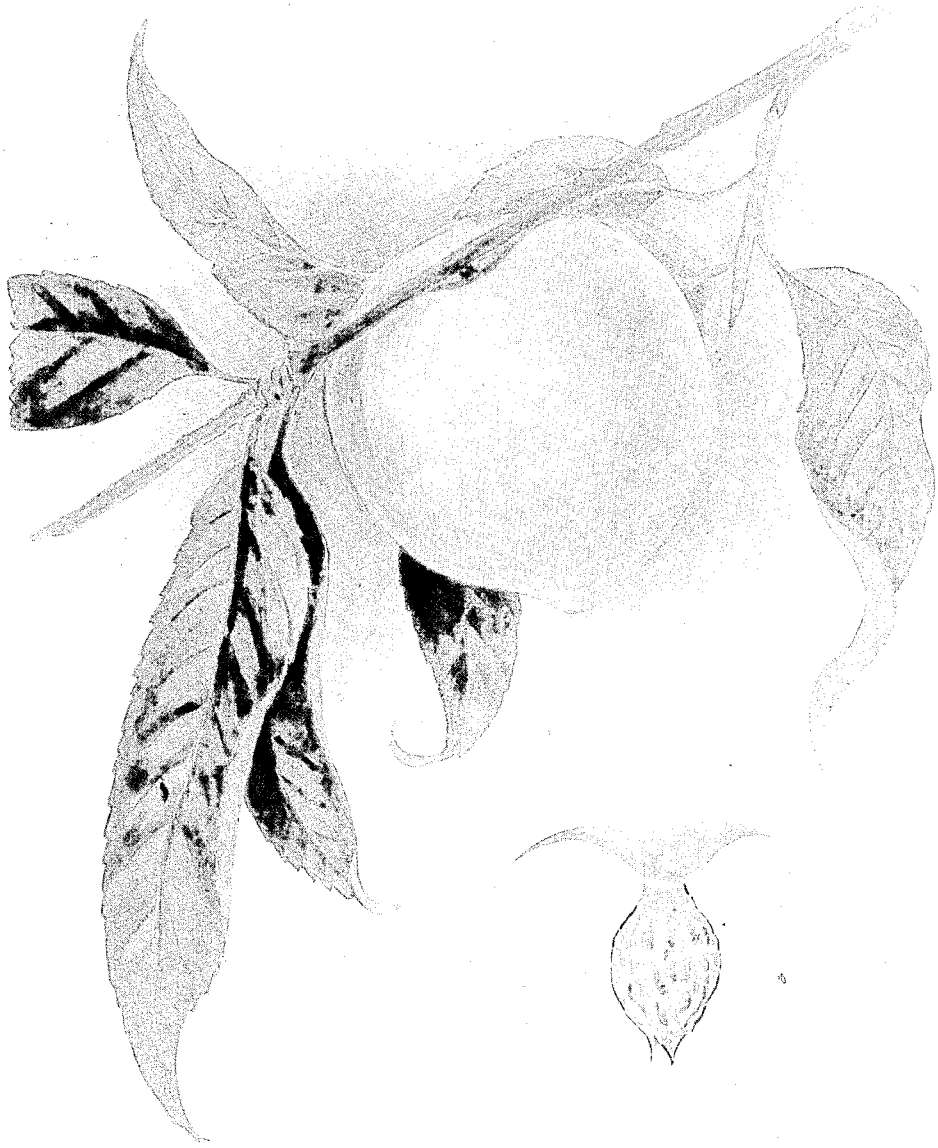
WITNESS
Addison J. Avery
INVENTOR
Grant Merrill
Webster & Webster
ATTYS Patented Aug. 30, 1949

Plant Pat. 869

UNITED STATES PATENT OFFICE

869

PEACH TREE

Grant Merrill, Red Bluff, Calif.

Application August 28, 1948, Serial No. 46,602

1 Claim. (Cl. 47—62)

This invention relates to a new and distinct variety of peach tree bearing semi-freestone fruit; the advantages of the variety, with respect to the fruit, being extremely early ripening as compared to other semi-freestone varieties, high color, excellent eating quality, and adaptability to reasonably long distance shipping.

The present variety of peach tree bears greater resemblance to the Arp than any other variety, but the fruit of the present variety ripens substantially in season with the Redbird variety.

Additionally, as compared to the Arp, the present variety of peach tree bears fruit which is firmer of flesh, with the flesh semi-free, while the Arp is a cling. Further, the fruit is oval and more pointed than the Arp.

This new and distinct variety of semi-freestone peach tree was originated by applicant on his ranch at Red Bluff, California, in the following manner:

Seeds were gathered from a J. H. Hale peach tree growing next to a block of many varieties of peaches, and such seeds were planted. From the resultant seedlings one was selected and planted in a test orchard, being identified in applicant's records as the C1–8. It is believed by applicant that the J. H. Hale was crossed with the Arp in producing the C1–8, as it and its progeny resemble the Arp. Pollinated seeds of the C1–8 variety were then planted, and of the resultant seedlings one was selected as of special merit, being the herein claimed variety, and known in applicant's records as the C4–3.

The variety, since its origination, has been successfully asexually propagated; having been budded in May 1943, and planted in January, 1944. Subsequently, asexually reproduced peach trees of the variety have come into bearing and are found to retain in full the novel characteristics of the original tree of the variety and the fruit thereof.

In the original drawings:

Fig. 1 is a perspective view of a fruit of the variety as attached to a twig with leaves.

Fig. 2 is a sectional view taken axially of the fruit, with the stone exposed.

Referring now in detail to the new and distinct variety of peach tree, the following is a detailed description, in outline, of such tree and its fruit:

*Tree*

Medium size; medium vigorous; medium upright; medium dense; vase formed; very productive; regular bearer.

Trunk: Medium stocky; medium shaggy.

Branches: Medium stocky; medium shaggy; reddish brown.

*Lenticels.*—Numerous; medium size.

Leaves: Length, 5¼ to 5½ inches; width 1¼ to 1½ inches; medium size; oval-lanceolate, acuminate; medium thickness; medium green; smooth.

*Margin.*—Finely crenate; glandular at base on most leaves.

*Petiole.*—Medium length; medium thickness.

*Glands.*—Average number, 2 to 5; on base of leaf, and upper petiole; medium size, alternate, few opposite; reniform; red color. Stipules—on very new growth, dropping off early.

Flower buds: Medium size; short; obtuse; free; very pubescent.

Flowers: Date first and full bloom—February 26 and March 10, 1948. Midseason; medium size; pink.

*Fruit*

Maturity when described, eating ripe. The date of first picking is in the period of June 10th to 15th, and the date of last picking is in the period of June 18th to 23rd; both dependent upon climatic conditions.

Size: Uniform, medium size. Diameter, axial, 2½; transverse in suture plane, $2\frac{5}{16}$. Transverse, cheek to cheek, $2\frac{5}{16}$.

Form: Uniform; oval; slightly unsymmetrical; not compressed.

Suture: Shallow, distinct; has slight depression toward pistil point.

Ventral surface: Very slightly lipped toward apex on one side.

Lips: Equal to slightly unequal.

Cavity: Elongated in suture plane with suture showing on both sides. Depth, $\frac{5}{16}$ inch; breadth, ½ inch. Markings—slightly spotted with red when fully ripe.

Base: Rounded.

Apex: Short; pistil point apical.

Skin: Medium thickness; medium toughness; not astringent or bitter; medium free from the flesh. Tendency to crack—none. Color—yellow under-color with red over-color with red splashes.

*Down.*—Moderate, short; rolls up when rubbed.

Flesh:

*Color.*—Light yellow, slightly red mottled on sunny side throughout.

*Surface of pit cavity.*—Yellow, with slight green tinge.
*Amygdalin.*—Scant.
*Juice.*—Abundant, rich.
*Texture.*—Medium soft, finely grained, melting.
*Fibres.*—Few, fine.
*Ripens.*—On apex first.
*Flavor.*—Mildly subacid.
*Aroma.*—Distinct.
*Eating quality.*—Good.

Stone: Semi-free, adheres to flesh over the lower halves of the sutures.
*Fibres.*—Medium.
*Free.*—Retains short, fiber-like threads and some flesh along ridges.
*Size.*—Medium.
*Length.*—1¼ inches.
*Breadth.*—⅞ inch.
*Thickness.*—¾ inch.
*Form.*—Obovate.
*Base.*—Straight.
*Hilum.*—Oval.
*Base.*—Straight.
*Apex.*—Short, acuminate.
*Sides.*—Equal, slightly flattened.
*Surface.*—Irregularly furrowed toward apex, ridged throughout. Pitted from base to above center.
*Ridges.*—Rounded toward apex.
*Pits.*—Circular.
*Ventral edge.*—Thick, wing toward base.
*Dorsal edge.*—Narrow with deep narrow groove to above center.
*Ridges.*—On either side, continuous or interrupted.
*Tendency to split.*—Only very slight.
*Color.*—Light tan.

The present variety of peach tree, described above, bears a substantial resemblance to the Arp, except that the tree is slightly less vigorous than the Arp. The fruit of the present variety of peach tree bears substantial resemblance to the fruit of the Arp, but is firmer, semi-free from the flesh, and more pointed.

The fruit is especially adaptable for dessert and culinary use; the market being local and middle distant. The fruit is capable of withstanding reasonably long distance shipping; the keeping quality being medium.

The variety has medium resistance to insects and diseases.

The advantages of the present variety are its extremely early ripening period for a semi-freestone peach, being in season with the Redbird; its high color—being yellow with red over-color and splashed in red—and its adaptability to reasonably long distance shipping, as aforesaid. To applicant's knowledge the present variety is the earliest semi-freestone known.

The tree and its fruit as herein described may vary in slight detail due to climatic and soil conditions under which the variety may be grown.

Having thus described my invention, I claim:

A new and distinct variety of peach tree characterized by its similarity to the Arp but having an extremely early ripening period which is substantially in season with the Redbird; the fruit being of high color, yellow with red over-color and splashed in red, semi-freestone and, as compared to the Arp, firmer but more free from the flesh, and more pointed in shape.

GRANT MERRILL.

No references cited.